United States Patent [19]
Brennan et al.

[11] Patent Number: 6,076,013
[45] Date of Patent: Jun. 13, 2000

[54] APPARATUS AND METHODS FOR TREATING CONGESTIVE HEART FAILURE

[76] Inventors: Edward F. Brennan, 1216 Arguello Blvd., San Francisco, Calif. 94122-2707; Daniel Burkhoff, 4 Marcotte La., Tenafly, N.J. 07670

[21] Appl. No.: 09/231,022

[22] Filed: Jan. 14, 1999

[51] Int. Cl.⁷ ........................................ A61N 1/36
[52] U.S. Cl. .................. 607/2; 601/153; 607/129
[58] Field of Search .................... 602/2, 9, 116, 602/119, 129, 16–17; 600/374; 601/153

[56] References Cited

U.S. PATENT DOCUMENTS

| | | | |
|---|---|---|---|
| 5,095,916 | 3/1992 | Smits | 607/116 |
| 5,533,958 | 7/1996 | Wilk | 601/153 |

*Primary Examiner*—William E. Kamm
*Attorney, Agent, or Firm*—Albert Keyack

[57] ABSTRACT

Apparatus and method for the treatment of congestive heart failure are disclosed that utilize a cuff that surrounds the heart and constrains cardiac dilation, while electrodes embedded in the cuff stimulate the myocardium to contractile function. An EKG signal can be processed to create an optimal pattern of selective stimulation of different areas of the heart at different times. An implantable circuit contains a power source and stimulation circuits. In some embodiments, a telemetry unit and an EKG collection circuit are also included. In accordance with the present disclosure, cuff limits the dilation of the heart and the stimulation electrodes enhance ventricular function by optimizing ventricular contractility.

24 Claims, 4 Drawing Sheets

APPARATUS AND METHODS FOR TREATING CONGESTIVE HEART FAILURE

The present invention relates to treating patients having congestive heart failure by mechanical and electrical therapy, and more specifically relates to using an implanted device to limit dilation and manage cardiac function by applying electrical impulses.

BACKGROUND OF THE INVENTION

Heart failure affects approximately three million Americans, and new cases of heart failure number about 400,000 each year. Congestive heart failure (CHF) is particularly insidious, affecting at least two million Americans, and is a syndrome characterized by left ventricular dysfunction, reduced exercise tolerance, impaired quality of life, and markedly shortened life expectancy. In patients suffering from CHF, decreased contractility of the left ventricle leads to reduced cardiac output with consequent systemic arterial and venous vasoconstriction. This vasoconstriction, which promotes the vicious cycle of further reductions of stroke volume followed by an increased elevation of vascular resistance, appears to be mediated, in part, by the renin-angiotensis system. The key component of this system, the potent vasoconstrictor angiotensin II, also has the effect of stimulating aldosterone secretion, possibly enhancing sympathetic drive and increasing vasopressin secretion. Cohn, J. N. et al., N. England J. Med. 325(5):303–310 (1991).

Drugs are sometimes employed to assist in treating problems associated with cardiac dilation. For example, digoxin increases the contractility of the cardiac muscle and thereby causes enhanced emptying of the dilated cardiac chambers. On the other hand, some drugs such as beta-blocking drugs decrease the contractility of the heart and therefore increase the likelihood of dilation. Other, pharmacological and/or biopharmaceutical treatments have been used previously. For example, angiotensin-converting enzyme (ACE) inhibitors, such as captopril and enalopril, have become standard therapy for patients with congestive heart failure. These drugs improve hemodynamic profile and exercise tolerance and reduce the incidence of morbidity and mortality in patients with congestive heart failure. However, despite these effects, the degree of clinical efficacy has been limited. Improvement in functional capacity and exercise time is small and mortality, although reduced, continues to be high. Moreover, many of these drugs have side effects which make them undesirable for long-term use.

Another approach has been to use a chronic hypersecretion of growth hormone (GH) in an attempt to induce a pattern of myocardial contraction that allows the cardiac muscle to function more economically. Timsit, J. et al., J. Clin. Invest. 86:507–515 (1990); Timsit, J. et al., Acta. Paediatr. Suppl. 383:32–34 (1992). The increase in the contractile performance was shown to be due to specific alterations in the properties of the contractile apparatus, including an increase in both maximal tension and myofibrillar sensitivity to calcium. Mayoux, E. et al., Circulation Research 72(1):57–64 (1993). Similarly, acute intravenous administration (infusion or bolus injection) of Insulin-like growth factor (IGF-I) produces increases in stroke volume and cardiac output in normal lambs. Gluckman et al., PCT WO 92/11865 (1992). It has also been suggested that improvement in cardiac performance for patients with congestive heart failure may be achieved by combining ACE inhibitors with a treatment regimen of GH and IGF-I. To date, however, none of the therapies discussed above have been approved for use in human patients.

Although a prominent symptom of CHF, cardiac dilation occurs as a result of many forms of cardiac disease. In some cases, such as post-myocardial infarction, the dilation may be localized to only a portion of the heart. In other cases, such as hypertrophic cardiomyopathy, there is typically increased resistance to filling of the left ventricle with concomitant dilation of the left atria. In dilated cardiomyopathy, the dilation is typically of the left ventricle with resultant decreased cardiac efficiency, and the continuing failure of the heart to adequately pump. With each type of cardiac dilation, there are associated problems ranging from arrhythmia which arise due to the stretch of myocardial cells, to leakage of the cardiac valves due to enlargement of the valvular annulus.

In addition to the treatments set forth above, devices to prevent or reduce cardiac dilation and thereby reduce the consequences of dilation are also know. For example, patches made from low porosity materials of the type used to repair cardiac ruptures and septal defects, such as Dacron™ have also been applied to support the cardiac wall where no penetrating lesion is present. This concept has been expanded to devices that attempt to constrain dilation. For example, U.S. Pat. No. 5,702,343—Alfernes, which is assigned to Acorn Medical, discloses a device applied to the epicardial surface of the heart for reinforcement of the cardiac wall during diastolic chamber filling to prevent or reduce cardiac dilation. The device includes a biomedical material applied to the epicardial surface that expands to a predetermined size to constrain cardiac expansion beyond a predetermined limit. The device may be a patch, or alternatively, a jacket with a predetermined size that surrounds the heart circumferentially. Similarly, U.S. Pat. No. 5,800,528—Lederman, et al. which is assigned to Abiomed R&D, Inc. discloses maintaining a passive girdle around a patient's heart and gradually reducing the size of the girdle to effect a constriction of the ventricle over time, thus preventing further dilation and attempting to reduce volume.

In addition to drugs and constraining structures, another method of treating CHF is by cardiac rhythm management devices such as dual chamber pacemakers. U.S. Pat. No. 5,800,471—Baumann, which is assigned to Cardiac Pacemakers, Inc. In the disclosed pacemaker, the pacing mode-AV delay is adjusted by sensing atrial and ventricular depolarization events to attempt to optimize hemodynamic performance. A similar dual chamber pacing system is disclosed n U.S. Pat. No. 5,749,906—Kieval et al., which is assigned to Medtronic, Inc. The dual pacing solution, although somewhat effective, has to date met with limited clinical success, largely due to the variability of the signals collected to determine the pacing mode.

Finally, treating CHF with invasive surgical remedies such as cardiomyoplasty has to date also led to little clinical gain. As explained in U.S. Pat. No. 5,738,626—Jarvik, cardiomyoplasty is a high mortality procedure with little clinical benefit (50% at two years) with limited hemodynamic benefit, and an even more radical approach—excision of a portion of the myocardium—is said to provide improved cardiac function although the mortality is still forty percent (40%) at one year. The Jarvik patent proposes a combination of excision followed by myoplasty. Others have suggested that the efficacy of myoplasty can be improved by the functional neuromuscular electrical stimulation of the transected skeletal muscle, e.g., U.S. Pat. No. 5,752,978—Chancellor.

Thus, there remains a long felt, yet to date unmet need to provide a therapeutic solution to minimize the deterioration of the heart associated with CHF.

Accordingly, it is an object of this invention to provide apparatus and methods whereby the heart is constrained from dilation.

It is another object of this invention to provide apparatus and methods that will assist physicians in collecting treatment data, as well as providing therapy.

SUMMARY OF THE INVENTION

It has now been found that these and other objectives can be met by a system for treating ventricular dilatation comprising a cuff disposed around the heart and a plurality of stimulation electrodes in contact with the heart. The cuff limits dilation and a stimulator sends one or more electrical impulses to the stimulation electrodes. The resulting focused electrical stimulation optimizes contractile force in the heart. The cuff is preferably constructed of a material that is biologically inert and is substantially inelastic so as to prevent further dilatation of the ventricle. The cuff preferably also has a section sized and configured to conform to a particular patient's cardiac anatomy and is made of an inelastic mesh or non-mesh material. It is preferred that the cuff be constructed so that a thoracoscopic instrument can be employed for implanting the cuff.

The stimulation electrodes are preferably in a matrix embedded within the cuff, and the surface of the electrodes make intimate contact with an exterior surface of the heart. Each of the stimulation electrodes is typically electrically isolated from other electrodes in the matrix. The electrode material is preferably chosen from materials that will not degrade with repeated electrical pulsation. In certain preferred embodiments, the detection electrodes selectively detect the physiological electrical signals associated with an EKG signal, and in some embodiments the stimulation electrodes themselves will comprise detection electrodes.

In some embodiments, a processor for analyzing electrical signals detected and determining a configuration for a pattern of electrical stimulation to optimize the efficiency of the resulting depolarization and ventricular contraction is also provided. Preferably, the processor is incorporated into an implantable electrical source, which may further have a telemetry circuit for communicating with an external console. The external console configures at least the temporal pattern and amplitude of the stimulating electrical pulses either as a result of manual inputs or automatically. Additionally, the circuitry provided has an algorithm to optimize temporal and spatial relationships between electrodes physically so that in time and sequence they are activated to optimize contractile force. In an additional aspect of the present invention, methods of treating congestive heart failure are also disclosed. In accordance with these methods, a cardiac reinforcement device is implanted and attached to an epicardial surface of the heart. The device comprises a cuff of inelastic material and a plurality of stimulation electrodes in contact with the heart. The cuff limits the dilation of the heart by circumferentially surrounding at least a portion of a ventricle, and stimulates contraction of the myocardium by activating the stimulation electrodes, improving ventricular function. In certain embodiments, an EKG signal is used to control the activation of the stimulation electrodes, and in some embodiments the EKG signal is collected by providing detectors as part of the cardiac reinforcement device. In certain embodiments, the device is placed around the heart using a thoratoscopy.

DETAILED DESCRIPTION OF THE PREFERRED EMBODIMENTS

Figure 1:
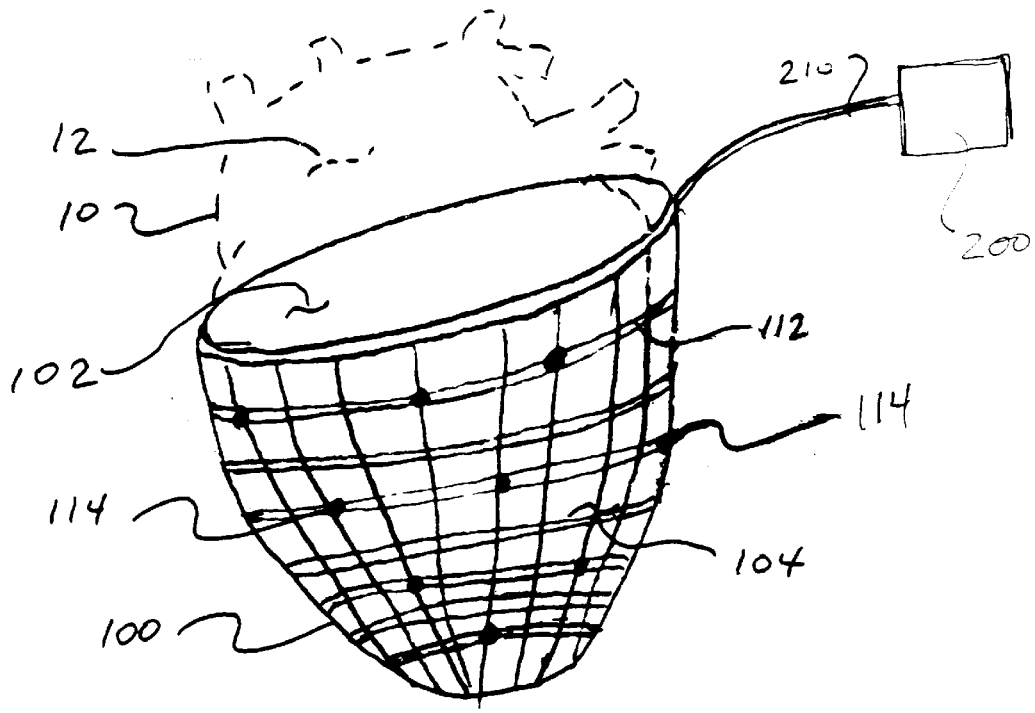
FIG. 1 is a perspective view of a cuff made in accordance with the present invention.

Referring now to FIG. 1, a perspective view, partially schematic, of a cuff 100 made in accordance with the present invention is shown. Preferably, the cuff 100 is comprised of a substantially inelastic material. The material of the cuff should most preferably be highly flexible and designed to be conformable to the shape of the heart 10, seen in phantom to more clearly illustrate the invention. It is particularly preferred that the material of the cuff 100 exhibit essentially no strain, whether elastic strain, inelastic strain or via hysteresis, and thereby precludes further dilatation of the heart 10. As used herein, the term "strain" is used in the sense of a ratio of unit change in length to total length. Another preferred characteristic of the material used to create the cuff 100 is that it have a low coefficient of friction and is substantially smooth on both the inner side 102 in contact with the epicardium 12 and the exterior side 104 in order to inhibit or at least minimize abrasions with body tissue so no focus for irritation and fibrosis is created. Those of skill in the art will also readily understand that the cuff 100 should be constructed of a material that is biocompatible and biologically inert and stable; it should not induce acute inflammation nor should it create a chronic immune response. Finally, as will be recognized by those of skill in the art, the material chosen should be capable of being sterilized by conventional methods such as gamma ray irradiation, ethylene oxide exposure or steam sterilization.

In accordance with the present invention and as illustrated in FIG. 1 the cuff 100 is preferably constructed to permit wires 112 and/or electrodes 114 to be imbedded between the outer surface 104 and the inner epicardium contacting surface 102. Preferably, the electrodes 114 are selectively exposed at particular regions of the interior surface 102 of the cuff 100 as explained in further detail below. The cuff 100 should be constructed in such a way that it can be attached to the heart 10, typically at the atrial-ventricle groove, or it is constructed such that it remains in position without direct attachment, e.g., via a suture.

Finally, as shown schematically in FIG. 1, a system 200 comprising a pacing detector circuit and a switch/detector circuit is connected via a cable 210 to the cuff 100 so that signals may be carried to and from the wires 112 and/or electrodes 114, as explained in further detail below. A battery (not illustrated) or other source of current is also provided.

Figure 2:
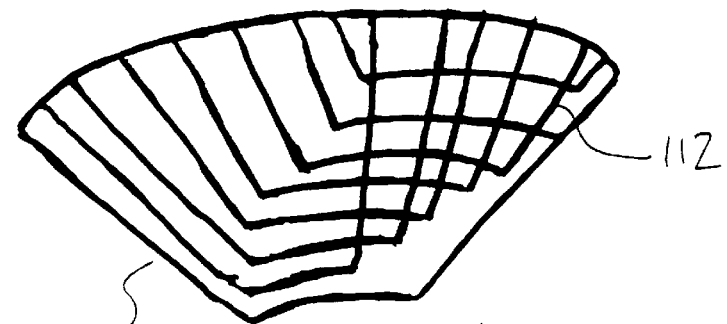
FIG. 2 is a plan view of a surface of the cuff illustrated in FIG. 1.
Figure 3:
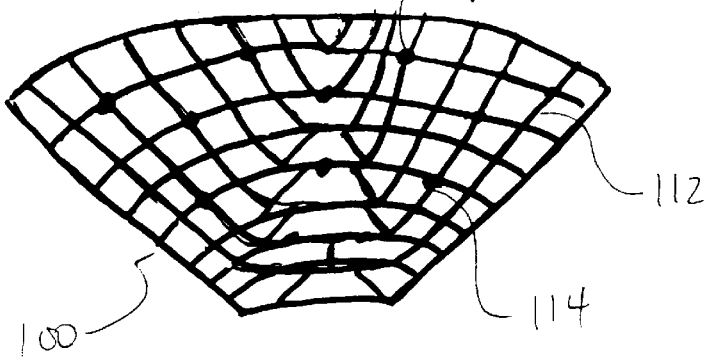
FIG. 3 is a plan view similar to FIG. 2 illustrating further details of the invention.

Referring now to FIG. 2, a surface related to the surface of one embodiment of a cuff 100 is illustrated. For purposes of illustration, only some of the wires 112 are illustrated and the electrodes 114 described above are removed. In FIG. 2 it can thus be seen that the wires are preferably laid in an orderly pattern that will result in well understood current paths. Referring now to FIG. 3, it can be appreciated that the electrodes 114 are formed along the current paths defined by the wires 112. The electrodes 112 are most preferably constructed of a material that with the proper electrical pulse characteristics charge balance will be obtained. For example, Platinum-Iridium alloy is such a material. The selection of such materials and the construction of an array of wires 112 or other conductors and electrodes 114 are well known in the art of cardiac pacing as well as the general art of stimulating muscles with electricity for therapeutic effect.

In some embodiments of the present invention, the electrodes 114 are capable of obtaining the electrical signals associated with the depolarization of the cardiac cells, normally represented in elctrocardiology as the electrocardiogram (EKG). Obtaining such signals with epicardial surface leads and processing the raw signal into a usable EKG trace is well known in the art. In accordance with the therapy of the present invention, the electrodes 114 also carry out a stimulation function, i.e., the electrodes 114 transmit electrical energy directly to the myocardium. This electrical stimulation of the myocardium, in conjunction with the mechanical restraint of the cuff 110 will act to prevent further dilation and control the electrical and mechanical responses of the dilated ventricle to attempt to restore a more normal cardiac function.

Figure 4:
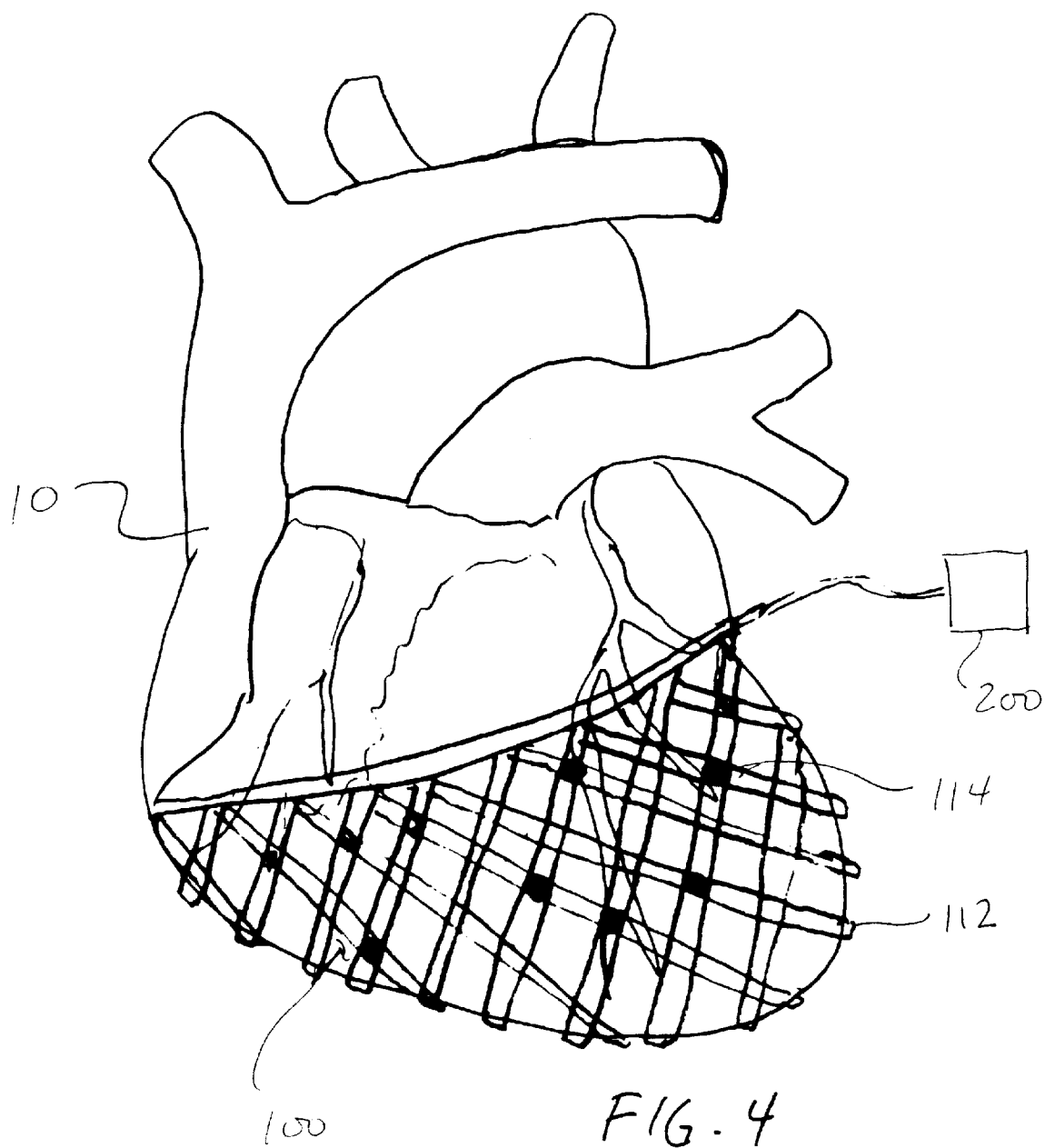
FIG. 4 is a perspective view of the embodiment illustrated in FIG. 1 after affixation to a heart.

Referring now to FIG. 4 while still referring to FIGS. 1–3, it can now be seen how the cuff 100 is fitted to the heart 10. As explained above, a circuit 200 is connected to the cuff 100. Part of the circuit 200 comprises a stimulator that is also capable of transmitting and receiving information from outside the body, i.e., via telemetry. Preferably, the stimulator and the rest of the circuit 200 is completely encased and implanted in the patent. The encased stimulator 200 produces electrical signals that are applied to the heart to facilitate, induce or optimize contraction of the ventricle(s). Pulses of differing voltage, current, duration and polarity are created and sent to the heart in accordance with the condition of the patient. In preferred embodiments, the shape of the electrical pulses should be configurable and designed to be effective with the design of the preferred design of the cuff 100 that has multiple contacts to which electrodes 114 can be individually connected. Most preferably and optimally, the stimulation pulses should be selectively transmitted to one or more particular electrodes 114 to deliver electrical energy in a precise manner. Providing electrical stimulation to the heart, pulse shaping and selective activation of ones of a plurality of electrodes are all well known in the arts of cardiology and cardiac electrotherapy.

As noted above with reference to the cuff 100, the encased circuit 200 should also be biocompatible and is therefore preferably constructed of a material that is biologically inert. It should not induce acute inflammation nor should it cause a chronic immune response. The encased circuit 200 should be constructed of a material capable of being sterilized by conventional methods such as gamma ray irradiation, ethylene oxide exposure or steam sterilization.

Figure 5:
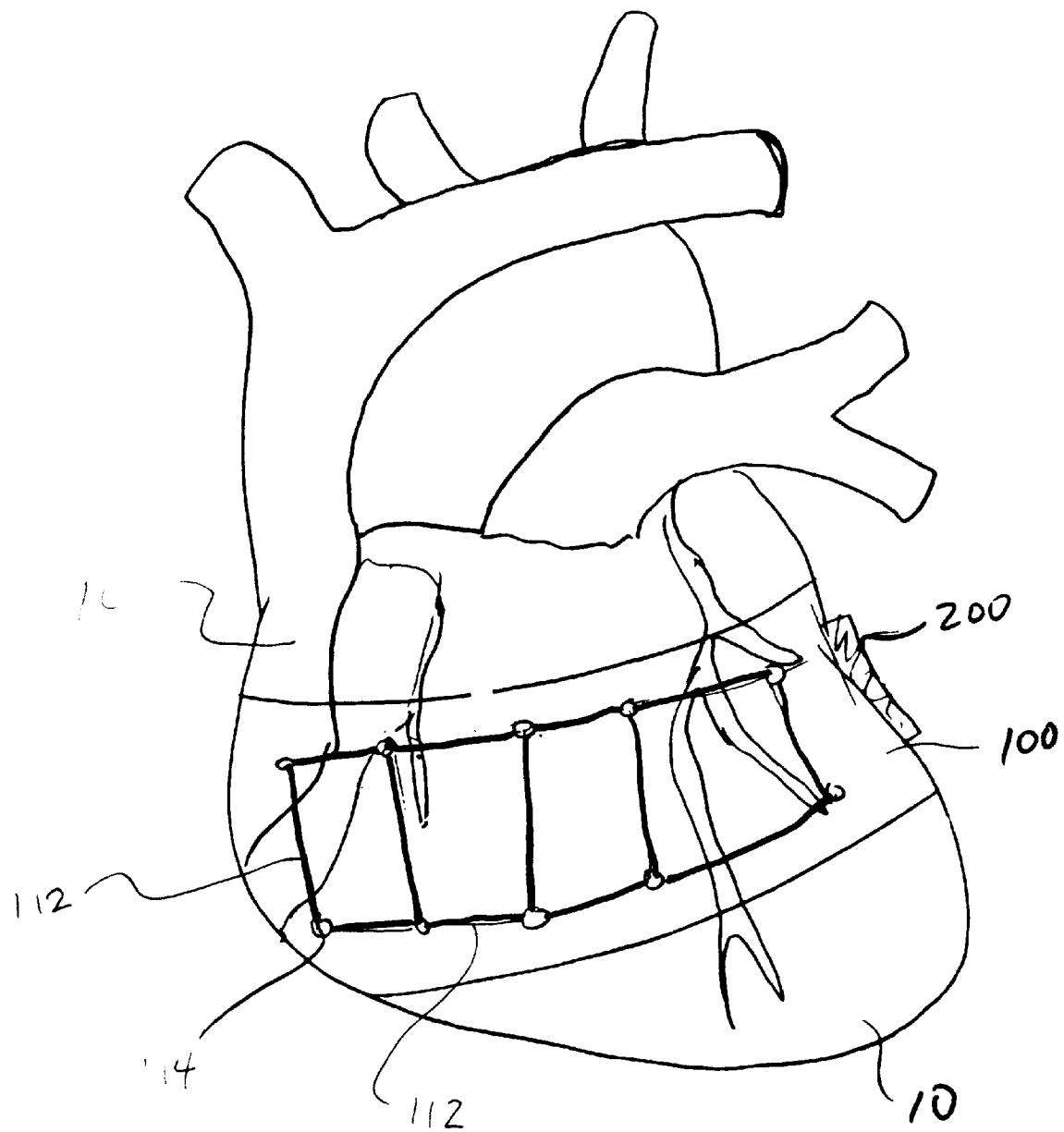
FIG. 5 is a perspective view similar to FIG. 4 illustrating an alternate embodiment of a cuff made in accordance with the present invention.

Referring now to FIG. 5, an alternate embodiment of a cuff 150 made in accordance with the present invention is illustrated in a manner substantially identical to that illustrated in FIG. 4. In this embodiment, however, the cuff 150 is a band or strip that is more generally open toward the apex of the heart 10, as illustrated. Thus, as used herein, the term "cuff" includes both structures that are completely closed at the apex and substantially enclose at least the ventricle of the heart and more open structures that encircle a portion of the ventricle, as seen in FIG. 5. Those of skill in the art will understand that there are a number of shapes that will be useful variants to the two embodiments illustrated. Moreover, it is also readily understood that the spacing and placement of the wires 112 and electrodes 114 described in detail above present an almost limitless variety of combinations of physical connectivity and selective activation, either as a stimulation point or, in some embodiments, a sensing point for an EKG signal.

Figure 6:
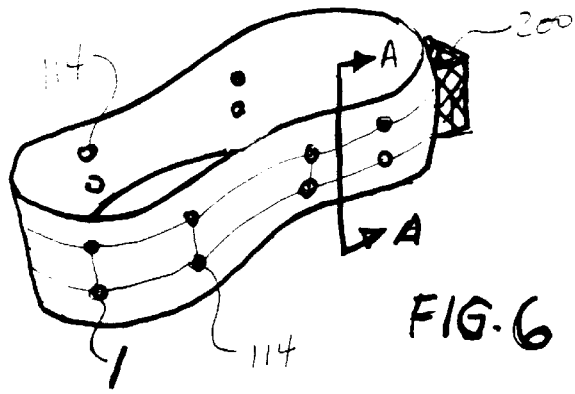
FIG. 6 is a perspective view of the cuff of FIG. 5 prior to affixation to a heart.
Figure 7:
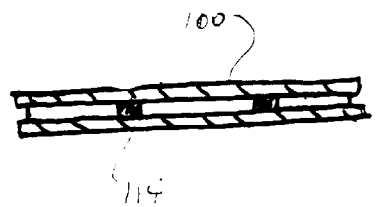
FIG. 7 is a cross-sectional elevation view taken along line A—A in FIG. 6 illustrating the construction of the cuff.

Referring now to FIG. 6 an isometric view of the cuff 150 shown in FIG. 5, removed from the heart is shown. FIG. 7 is a cross-section of the cuff 150 taken along line A—A shown in FIG. 6. As illustrated, the preferred construction of the cuff 150 (or any other cuff design) is a laminated structure comprising at least a layer of inelastic material and a layer of embedded wires 112 and electrodes 114.

Figure 8:
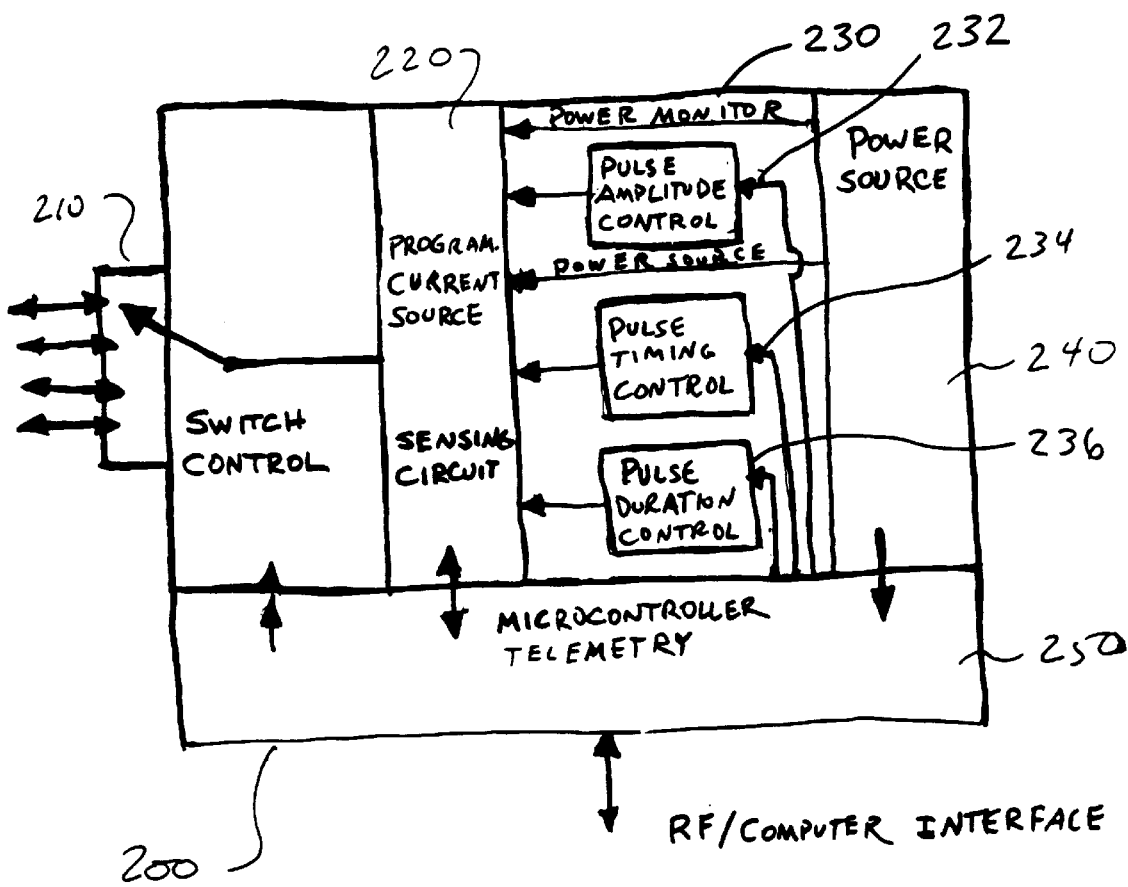
FIG. 8 is a functional block diagram illustrating the circuits and signals used in certain embodiments of the present invention.

FIG. 8 illustrates a functional block diagram detailing the circuitry 200 described above. A switch control circuit 210 permits the selective connection of one or more of the wires 112 in cooperation with a programmable current source and sensing circuit 220. The programmable current source and sensing circuit 220 responds to a plurality of inputs, including power monitoring signals 230, pulse amplitude control signals 232, pulse timing control signals 234, and pulse duration control signals 236, as well as a power source input 240. Additionally, the switch control circuit 210, programmable current source and sensing circuit 220, and power source 240, such as a battery, are all in communication with signals from a microcontroller and with a telemetry unit 250, which transmits and receives a signal that manages the application of energy to the electrodes based on, for example, an EKG signal.

A cuff made in accordance with the present invention can be affixed to the heart in a number of ways. Preferably, the cuff is designed so that a drawstring can be used to capture the open end (basal) in the AV groove usually present on the surface of the heart. Additionally, in some embodiments, the cuff will be shaped so that it can be folded and deployed more easily using thoratascopic technique.

Although specific embodiments of the present invention have been specifically described, the invention is not limited to such embodiments. Upon review of the foregoing description, adaptations, modifications, variations and alternatives that utilize the spirit of the invention embodied herein will occur to those of skill in the art.

What is claimed is:

1. A system for treating ventricular dilatation, comprising:
   (a) a cuff disposed around at least a portion of a heart comprised of:
      a substrate; and
      a plurality of stimulation electrodes in contact with the heart, wherein the cuff limits the dilation of the heart; and
   (b) a stimulator that sends one or more electrical impulses to one or more of the stimulation electrodes,
      whereby focused electrical stimulation of the heart optimizes contractile force in the heart.

2. The system of claim 1, wherein the cuff is constructed of a biologically inert material and is substantially inelastic, whereby the cuff will not allow further dilatation of the ventricle.

3. The system of claim 1 wherein the plurality of stimulation electrodes comprises a matrix of electrodes embedded within the substrate, and the surface of the electrodes are in contact with an exterior surface of the heart.

4. The system of claim 3 wherein each of the stimulation electrodes is electrically isolated from other electrodes in the matrix.

5. The system of claim 1 wherein the electrode material is chosen from materials that will not degrade with repeated electrical pulsation.

6. The system in accordance with claim 1, further comprising detection electrodes to selectively detect the physiological electrical signals associated with an EKG signal of the heart.

7. The system in accordance with claim 6, wherein the stimulation electrodes comprise detection electrodes.

8. The system of claim 6 further comprising a processor for analyzing electrical signals and determining a configuration for a pattern of electrical stimulation to optimize the efficiency of the resulting depolarization and ventricular contraction.

9. The system of claim 8 wherein the processor is incorporated into an implantable electrical source.

10. The system of claim 8 further comprising a telemetry circuit for communicating with an external console, whereby the external console configures at least the temporal pattern and amplitude of the stimulating electrical pulses.

11. The system of claim 10, wherein the external console configures the pulses as a result of manual inputs.

12. The system of claim 10, wherein the external console configures the pulses automatically.

13. The system of claim 1 wherein the cuff further comprises a conformable section sized and configured to conform to a patient's cardiac anatomy.

14. The system of claim 1, wherein the cuff is open ended.

15. The system of claim 1, wherein the cuff is closed ended.

16. The system of claim 1, wherein the cuff comprises an inelastic mesh material.

17. The system of claim 1, wherein the cuff comprises a inelastic non-mesh material.

18. The system of claim 1, further comprising a thoracoscopic instrument for implanting the cuff.

19. The system of claim 1, wherein the circuit comprises an algorithm to optimize temporal and spatial relationships between electrodes, whereby they are activated to optimize contractile force.

20. A cardiac reinforcement device, said device comprising:
   a cuff of a biomedical material for application to an epicardial surface of a heart to surround the epicardial surface and constrain cardiac expansion beyond a predetermined limit, said cuff comprising a base end, said base end having an opening for applying said cuff to the heart such that when applied the base end is oriented toward the base of the heart; and
   a plurality of stimulation electrodes in contact with the heart,
   whereby the cuff limits the dilation of the heart and the stimulation electrodes enhance ventricular function by optimizing ventricular contractility.

21. A method of treating congestive heart failure comprising the steps of:
   attaching a cardiac reinforcement device to an epicardial surface of the heart, the device comprising a cuff of inelastic material and a plurality of stimulation electrodes placed in contact with the heart;
   limiting the dilation of the heart by circumferentially surrounding at least a portion of a ventricle with the cuff; and
   stimulating contraction of the myocardium by activating the stimulation electrodes,
   whereby ventricular function is improved.

22. The method of claim 21, further comprising the step of creating an EKG signal and controlling the activation of the stimulation electrodes using the EKG signal.

23. The method of claim 22, wherein the step of creating an EKG signal comprises providing detectors as part of the cardiac reinforcement device.

24. The method of claim 21, wherein the step of inserting comprises placing the device around the heart using a thoratoscopy.

* * * * *